US011333631B2

(12) United States Patent
Yamanaka et al.

(10) Patent No.: US 11,333,631 B2
(45) Date of Patent: May 17, 2022

(54) SYSTEM, METHOD AND COMPUTER PROGRAM PRODUCT FOR MEASURING GAS CONCENTRATION

(71) Applicant: Ball Wave Inc., Sendai (JP)

(72) Inventors: Kazushi Yamanaka, Sendai (JP); Shingo Akao, Sendai (JP); Nobuo Takeda, Sendai (JP); Toshihiro Tsuji, Sendai (JP); Toru Oizumi, Sendai (JP); Yusuke Tsukahara, Sendai (JP)

(73) Assignee: BALL WAVE INC., Sendai (JP)

( * ) Notice: Subject to any disclaimer, the term of this patent is extended or adjusted under 35 U.S.C. 154(b) by 652 days.

(21) Appl. No.: 16/347,598

(22) PCT Filed: Nov. 6, 2017

(86) PCT No.: PCT/JP2017/039994
§ 371 (c)(1),
(2) Date: May 6, 2019

(87) PCT Pub. No.: WO2018/084296
PCT Pub. Date: May 11, 2018

(65) Prior Publication Data
US 2019/0360966 A1    Nov. 28, 2019

Related U.S. Application Data

(60) Provisional application No. 62/418,428, filed on Nov. 7, 2016.

(51) Int. Cl.
*G01N 29/036* (2006.01)
*G01N 29/02* (2006.01)
(Continued)

(52) U.S. Cl.
CPC ........... *G01N 29/036* (2013.01); *G01N 29/02* (2013.01); *G01N 29/022* (2013.01);
(Continued)

(58) Field of Classification Search
CPC .... G01N 29/022; G01N 29/02; G01N 29/024; G01N 29/036; G01N 33/0004;
(Continued)

(56) References Cited

U.S. PATENT DOCUMENTS

2006/0230834 A1   10/2006  Liu et al.
2007/0041870 A1*  2/2007  Yamanaka ......... G01N 29/2462
                                                  422/82.01
(Continued)

FOREIGN PATENT DOCUMENTS

JP    2012-042430 A    3/2012
WO    2016/084917 A1   6/2016

OTHER PUBLICATIONS

Kazushi Yamanaka et al., "Ultramultiple Roundtrips of Surface Acoustic Wave on Sphere Realizing Innovation of Gas Sensors", Institute of Electrical and Electronics Engineers (IEEE) Transactions on Ultrasonics, Ferroelectrics, and Frequency Control, Apr. 2006, pp. 793, vol. 53. Cited in the Specification.

(Continued)

*Primary Examiner* — Benjamin R Schmitt
(74) *Attorney, Agent, or Firm* — Metrolex IP Law Group, PLLC

(57) ABSTRACT

System and method for measuring a gas concentration are provided. A ball sensor generates a collimated beam of a surface acoustic wave including fundamental wave of first frequency and harmonic wave of second frequency, which propagates through a orbital path on piezoelectric ball while passing through sensitive film to adsorb a target gas. Temperature control unit controls ball temperature of the ball sensor. Signal processing unit transmits a burst signal to sensor electrode of the ball sensor to excite the collimated beam, receives burst signals after the collimated beam has propagated a predetermined number of turns around the piezoelectric ball, and calculates the gas concentration and (Continued)

the ball temperature by first and second relative changes in delay times of the first and second frequencies, respectively, using waveform data of the burst signals.

20 Claims, 13 Drawing Sheets

(51) Int. Cl.
*G01N 29/024* (2006.01)
*G01N 33/00* (2006.01)

(52) U.S. Cl.
CPC ....... *G01N 29/024* (2013.01); *G01N 33/0004* (2013.01); *G01N 33/0009* (2013.01); *G01N 2291/011* (2013.01); *G01N 2291/014* (2013.01); *G01N 2291/021* (2013.01); *G01N 2291/02809* (2013.01); *G01N 2291/0423* (2013.01)

(58) Field of Classification Search
CPC ......... G01N 33/0009; G01N 2291/011; G01N 2291/014; G01N 2291/021; G01N 2291/02809; G01N 2291/0423
See application file for complete search history.

(56) References Cited

U.S. PATENT DOCUMENTS

| | | | |
|---|---|---|---|
| 2010/0018288 A1* | 1/2010 | Yamanaka | G01N 30/76 73/24.02 |
| 2017/0307567 A1 | 10/2017 | Yamanaka et al. | |

OTHER PUBLICATIONS

Toshihiro Tsuji et al., "Burst waveform undersampling circuit for ball surface acoustic wave sensor", Proceedings of Symposium on Ultrasonic Electronics, Nov. 5-7, 2015, 3P3-6-1-2, vol. 36 (2015), Cited in the Specification.

Kazushi Yamanaka et al., "Simultaneous measurement of gas concentration and temperature by the ball SAW sensor", Proceedings of Symposium on Ultrasonic Electronics, Nov. 16-18, 2016, 3E2-4, vol. 37 (2016), Cited in the ISR.

Kazushi Yamanaka et al., "Simultaneous measurement of gas concentration and temperature by the ball surface acoustic wave sensor", Japanese Journal of Applied Physics, 2016, p. 07JC04-1-p. 07JC04-6, vol. 56, The Japan Society of Applied Physics; Cited in the EESR issued on Oct. 9, 2020.

An extended European search report (EESR) dated Oct. 9, 2020 in a counterpart European patent application.

\* cited by examiner

| w(ppbv) | Delta-$t_w$ | |
|---|---|---|
| | $T_B=14°C$ | $T_B=24°C$ |
| 1.3 | −0.65 | −0.36 |
| 234 | −6.13 | −3.33 |
| 590 | −8.94 | −5.94 |
| 1180 | −12.7 | −8.56 |

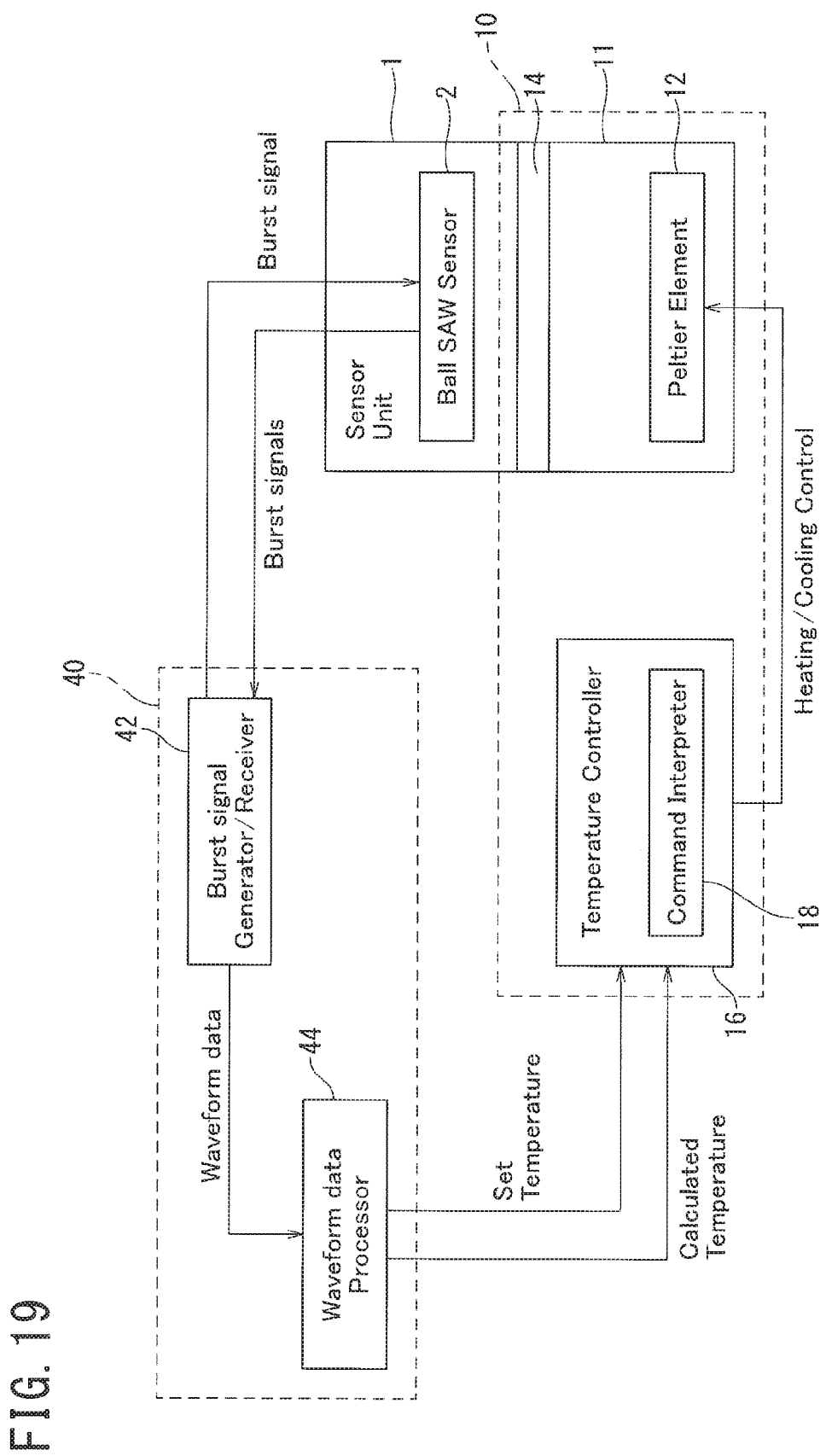
F I G. 19

SYSTEM, METHOD AND COMPUTER PROGRAM PRODUCT FOR MEASURING GAS CONCENTRATION

TECHNICAL FIELD

The present invention relates to a system, a method and a computer program product for simultaneously measuring a gas concentration and a ball temperature using a ball surface acoustic wave (SAW) sensor.

BACKGROUND ART

Earlier piezoelectric gas sensors, such as planar SAW sensors, utilize the propagation property that amplitude and phase of the exited SAW change when passing through a sensitive film in which elastic characteristics are changed by adsorbing gas molecules. However, diffraction occurs when waves of a finite width are propagating, and the SAW on the planar SAW sensor is attenuated by diffraction loss. Therefore, because of the diffraction loss, there is a limit to the propagation distance of the SAW, and measurement accuracy of gas concentration is limited.

As recited in non-patent literatures (NPLs) 1 and 2, a ball SAW sensor (hereinafter called "ball sensor") has been developed and applied to a trace moisture sensor. In the ball sensor, the SAW excited on a spherical surface with a specific condition may be naturally collimated, and multiple roundtrips along the equator of the ball can be realized. Thus, the ball sensor based on this effect may provide high performance, such as high sensitivity and wide sensing range.

Since the sensitivity of the piezoelectric gas sensor also depends on temperature of the sensor, measured gas concentration is disturbed when the sensor temperature is largely changed. However, it is not easy to measure the sensor temperature, when it is not possible to insert a thermometer into the sensor cell. The ball sensor also has the same problem.

CITATION LIST

Non Patent Literature

[NPL 1] K. Yamanaka, et al.: Institute of Electrical and Electronics Engineers (IEEE) Transactions on Ultrasonics, Ferroelectrics, and Frequency Control, vol. 53 (2006) pp. 793

[NPL 2] T. Tsuji, et al.: Proceedings of Symposium on Ultrasonic Electronics, 36 (2015) 3P3-6-1-2

SUMMARY OF INVENTION

Technical Problem

In view of the above problems, an object of the present invention is to provide a system, a method and a computer program product for measuring a gas concentration, which can simultaneously measure the ball temperature of the ball sensor and the gas concentration, with high sensitivity and reliability even under varying temperature.

Solution to Problem

A first aspect of the present invention inheres in a system for measuring a gas concentration, which encompasses a ball sensor and a signal processing unit. Here, the ball sensor has (a) a piezoelectric ball, (b) a sensor electrode configured to generate a collimated beam of a surface acoustic wave including a fundamental wave of a first frequency and a harmonic wave of a second frequency, which propagates through an orbital path on the piezoelectric ball, and (c) a sensitive film deposited on the piezoelectric ball, configured to adsorb a target gas, the sensitive film is arranged in a position where the collimated beam of the surface acoustic wave passes through. And the signal processing unit has (d) a signal generator configured to transmit a burst signal to the sensor electrode so as to excite the collimated beam propagating around the piezoelectric ball, (e) a signal receiver configured to receive burst signals of the collimated beam through the sensor electrode after the collimated beam has propagated a predetermined number of turns around the piezoelectric ball, and (f) a waveform data processor configured to calculate the gas concentration of the target gas and the ball temperature by first and second relative changes in delay times of the first and second frequencies, respectively, using waveform data of the burst signals.

A second aspect of the present invention inheres in a method for measuring a gas concentration using a ball sensor having a sensor electrode generating a surface acoustic wave and a sensitive film adsorbing a target gas, on a piezoelectric ball. The method pertaining to the second aspect of the present invention includes (a) flowing a gas containing the target gas into a sensor cell having the ball sensor in place, (b) transmitting a burst signal to the sensor electrode so as to excite a collimated beam of the surface acoustic wave including a fundamental wave of a first frequency and a harmonic wave of a second frequency, which propagates repeatedly through an orbital path on the piezoelectric ball while passing through the sensitive film deposited on the orbital path, (c) receiving burst signals of the collimated beam through the sensor electrode after the collimated beam has propagated a predetermined number of turns around the piezoelectric ball, and (d) calculating first and second relative changes in delay times of the first and second frequencies, respectively, by waveform data of the burst signals so as to calculate the gas concentration of the target gas and the ball temperature.

A third aspect of the present invention inheres in a computer program product embodied on a computer-readable medium for measuring a gas concentration using a ball sensor having a sensor electrode generating a surface acoustic wave and a sensitive film adsorbing a target gas, on a piezoelectric ball. The computer program product pertaining to the third aspect of the present invention includes (a) instructions to flow a gas containing the target gas into a sensor cell having the ball sensor in place, (b) instructions to transmit a burst signal to the sensor electrode so as to excite a collimated beam of the surface acoustic wave including a fundamental wave of a first frequency and a harmonic wave of a second frequency, which propagates repeatedly through an orbital path on the piezoelectric ball while passing through the sensitive film deposited on the orbital path, (c) instructions to receive burst signals of the collimated beam through the sensor electrode after the collimated beam has propagated a predetermined number of turns around the piezoelectric ball, and (d) instructions to calculate first and second relative changes in delay times of the first and second frequencies, respectively, by waveform data of the burst signals so as to calculate the gas concentration of the target gas and the ball temperature.

Advantageous Effects of Invention

According to the present invention, it is possible to provide the system, the method and the computer program product for measuring gas concentration, which can simultaneously measure the ball temperature of the ball sensor and the gas concentration, with high sensitivity and reliability even under varying temperature.

BRIEF DESCRIPTION OF DRAWINGS

FIG. 19 is a block diagram illustrating an example of temperature control and signal transmission in a system for measuring the water concentration according to a second embodiment of the present invention:

DESCRIPTION OF EMBODIMENTS

Figure 1:
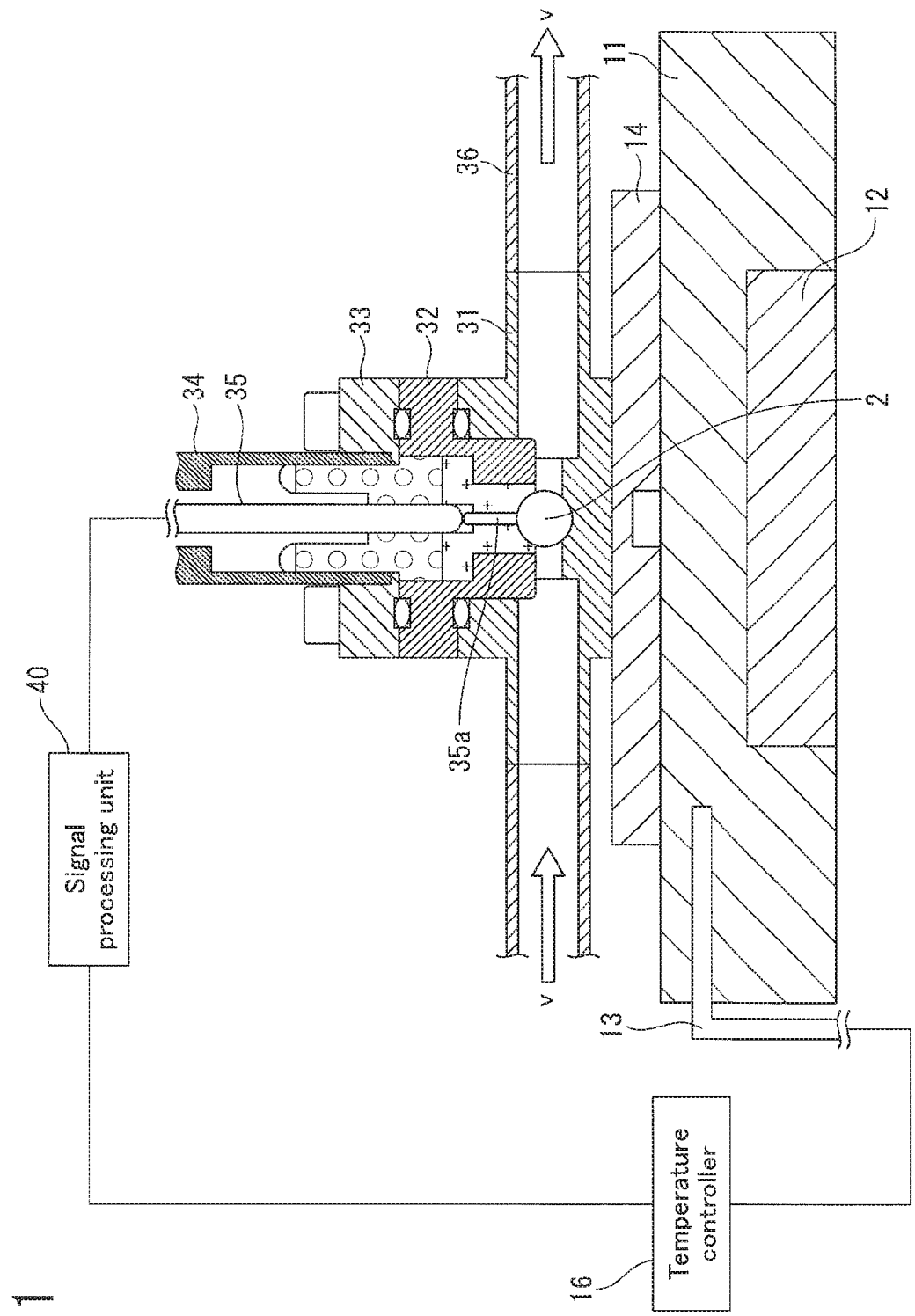
FIG. 1 is a schematic cross sectional view illustrating an example of a system for measuring water concentration according to a first embodiment of the present invention.

First and second embodiments of the present invention will be described below with reference to the drawings. In the descriptions of the following drawings, the same or similar reference numerals are assigned to the same or similar portions. However, the drawings are diagrammatic, and attention should be paid to a fact that the relations between thicknesses and plan view dimensions, the configuration of the apparatus and the like differ from the actual data. Thus, the specific thicknesses and dimensions should be judged by considering the following descriptions. Also, even between the mutual drawings, the portions in which the relations and rates between the mutual dimensions are different are naturally included. Also, the first and second embodiments as described below exemplify the apparatuses and methods for embodying the technical ideas of the present invention, and in the technical ideas of the present invention, the materials, shapes, structures, arrangements and the like of configuration parts are not limited to the followings. In the following description, the "horizontal" direction or the"vertical" direction is simply assigned for convenience of explanation and does not limit the technical spirit of the present invention. Therefore, for example, when the plane of paper is rotated 90 degrees, the "horizontal" direction is changed to the"vertical" direction and the"vertical" direction is changed to the "horizontal" direction. When the plane of paper is rotated 180 degrees, the "left" side is changed to the "right" side and the "right" side is changed to the "left" side. Therefore, various changes can be added to the technical ideas of the present invention, within the technical scope prescribed by claims.

First Embodiment (System Configuration)

Figure 2:
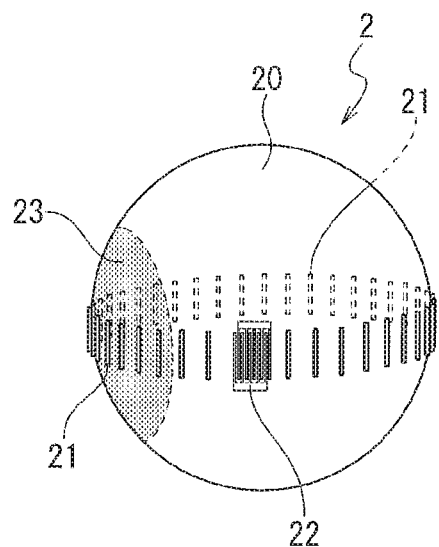
FIG. 2 is a schematic view illustrating an example of a ball sensor used in the system for measuring the water concentration according to the first embodiment of the present invention.

As illustrated in FIGS. 1 and 2, a system for measuring water concentration pertaining to a first embodiment of the present invention includes a sensor unit 1, a temperature controller 16, and a signal processing unit 40. The sensor unit 1 has a ball sensor 2 embedded in a tubular sensor cell 31, which is fixed on a plate-shaped adapter 14 disposed on a block-shaped holder 11. As the ball sensor 2 has spherical shape, with a tubular configuration, the inner structure of the sensor cell 31 has a concave configuration for mounting a lower portion of the ball sensor 2. An electrode-holder base 32 is fixed on the sensor cell 31, such that the bottom of the electrode-holder base 32 is inserted in an inner wall of a window, which is vertically cut at the top wall of the tubular sensor cell 31. An opening of a canal, which penetrates vertically through the bottom of the electrode-holder base 32, partially covers an upper portion of the ball sensor 2. Furthermore, the electrode-holder base 32 is capped by a sensor-cell cap 33.

The ball sensor 2 is connected to a rod-shaped external electrode 35 through a contact pin 35a along a vertical direction via the canal at the bottom of the electrode-holder base 32. The external electrode 35 is held in a hollow space of a vertically aligned cylindrical electrode holder 34, the bottom of which is inserted in an inner portion of the sensor-cell cap 33. A gas-containing trace-moisture or "the target gas-to-be-measured" is introduced into the sensor cell 31 through a horizontally aligned tubing 36 with a gas flow rate v, so that the target gas-to-be-measured can touch the surface of the ball sensor 2. The gas flow rate v is typically 0.1 L/min to 1 L/min.

As illustrated in FIG. 2, the ball sensor 2 may have a sensor electrode 22 and a sensitive film 23, which are arranged in predetermined areas on the surface of a homogeneous piezoelectric ball 20. As a three-dimensional base body, the piezoelectric ball 2 provides a homogeneous material sphere, on which a circular orbital band for propagating a SAW can be defined. The sensor electrode 22 generates a collimated beam 21 of the SAW, which includes a fundamental wave of a first frequency and a harmonic wave of a second frequency, propagates repeatedly through the circular orbital path defined on the piezoelectric ball 20 while passing through the sensitive film 23 deposited on the orbital path. The sensitive film 23 can be formed on almost the entire surface of the orbital band, which defines the orbital path on the three-dimensional base body. Because the sensitive film 21 is configured to react with specific gas molecules, the sensitive film 21 adsorbs water vapor in the target gas-to-be-measured.

For the piezoelectric ball 20, a crystal sphere, such as quartz, langasite ($La_3Ga_5SiO_{14}$), lithium niobate ($LiNbO_3$), lithium tantalate ($LiTaO_3$), piezoelectric ceramics (PZT), bismuth germanium oxide ($Bi_{12}GeO_{20}$) and the like, may be used. For the sensitive film 23, a silica ($SiO_x$) film and the like may be used. The sensor electrode 22 may be deposited in an opening of the sensitive film 23, the opening exposes a part of the surface of the piezoelectric ball 20, in a configuration such that the opening is formed on a part of the equator of the homogeneous piezoelectric ball 20. For the sensor electrode 22, an interdigital electrode (IDT) using a chromium (Cr) film and the like may be used as an electroacoustic transducer. In the case of a sphere of single crystal such as the homogeneous piezoelectric ball 20, a SAW orbiting route is limited to a specific orbital band having a constant width, depending on type of crystal material. The width of the orbital band may be increased or decreased depending on anisotropy of the crystal.

There are no diffraction losses during roundtrips around the piezoelectric ball 20, and only propagation loss due to material attenuation. The collimated beam 21 is scheduled to propagate many turns passing through the sensitive film 23, which is configured to adsorb water molecules. Because the adsorbed water molecules change the propagation characteristic of the SAW, the changes due to adsorbed water molecules on the sensitive film 23 can be integrated every turn through the multiple roundtrips. Thus, even though the sensitive film 23 may be so thin as to adsorb the small amount of the water vapor, measurement accuracy of water concentration may be increased.

The suitable relationship between the first frequency $f_1$ of the fundamental wave and the second frequency $f_2$ of the harmonic wave shall be represented by $f_2=nf_1$, where n=3 or 5. That is, in the system for measuring water concentration pertaining to the first embodiment of the present invention, the harmonic wave is the third-order harmonic wave or the fifth-order harmonic wave. Thus, when the first frequency $f_1$ is 80 MHz, the second frequency $f_2$ is 240 MHz for the third-order harmonic wave or 400 MHz for the fifth-order harmonic wave. Appropriate range of the first frequency $f_1$ for the piezoelectric ball 20 of 3.3 millimeters diameter may be from 60 MHz to 100 MHz, and the most suitable first frequency $f_1$ may be 80 MHz. The first frequency $f_1$ is inversely proportional to the diameter of the piezoelectric ball 20.

Figure 3:
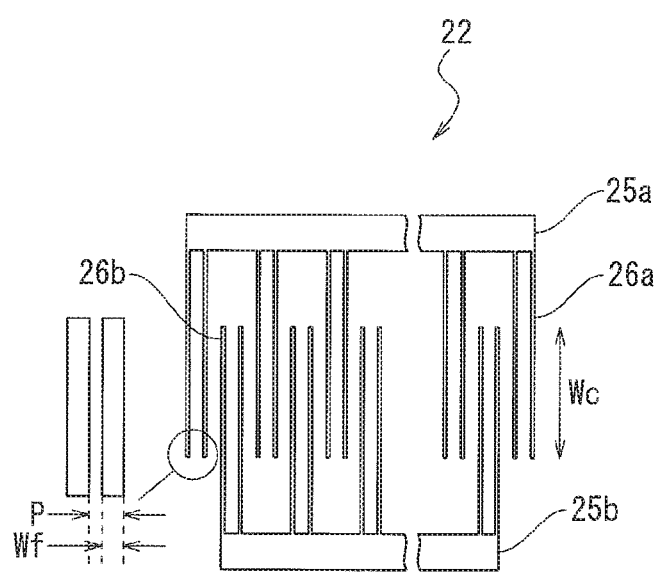
FIG. 3 is a schematic view illustrating an example of a sensor electrode of the ball sensor used in the system for measuring the water concentration according to the first embodiment of the present invention.

For example, the ball sensor 2 may be fabricated as described below. A pattern of an IDT of about 150 nanometers thick Cr film is deposited on a surface of a quartz ball having a diameter of 3.3 millimeters. As illustrated in FIG. 3, the IDT has a pair of bus bars 25a, 25b, and a plurality of electrode fingers 26a, 26b extending from the bus bars 25a, 25b, respectively. The electrode fingers 26a, 26b overlap each other with a cross width Wc, and each electrode finger 26a, 26b has a width Wf and a periodicity P. The cross width Wc, the width Wf and the periodicity P are designed as 364 micrometers, 6.51 micrometers and 10.0 micrometers, respectively, for the natural collimation of 80 MHz SAW (refer to NPL 1).

This IDT on the quartz ball having 3.3 millimeters diameter can generate 80 MHz SAW as a fundamental wave and 240 MHz SAW as a third-order harmonic wave. Then a silica film is synthesized by using a sol-gel method and coated on the surface of the quartz ball as follows: 3.47 grams of tetraethoxysilane (TEOS), 0.75 grams of isopropanol (IPA), and 1.50 grams of 0.1N hydrochloric acid (HCl) are mixed and stirred by sonication (27, 45, 100 kHz, 60 minutes). TEOS is polymerized by hydrolysis and resulted in $SiO_x$. After sonication, the mixture is diluted with IPA and 0.5 mass % $SiO_x$ solution is obtained. The surface of propagation route of SAW is coated with the $SiO_x$ solution using a spin coating. Condition of the spin coating is 3000 rpm for 20 seconds. The thickness of $SiO_x$ film is confirmed as 1029 nanometers from measurement using interference microscope.

An RF voltage is applied to the sensor electrode 22 via an electrode pad (not illustrated) arranged around the north pole (top of the piezoelectric ball 20 in FIG. 2) using the contact pin 35a attached on the bottom of the external electrode 35. Another electrode pad (not illustrated) arranged around the south pole (bottom of the piezoelectric ball 20 in FIG. 2) is in contact with the grounded sensor cell 31.

As illustrated in FIG. 1, the temperature controller 16 is connected to a Peltier element 12, which is held in a lower portion of the holder 11 at a position just below the ball sensor 2, and a thermistor 13 is inserted in the holder 11 at a side position of the holder 11. Furthermore, a temperature controller 16 is connected to the thermistor 13. The Peltier element 12 is used for heating and cooling the ball sensor 2 in the sensor cell 31 through the adapter 14. The thermistor 13 is used for detecting a monitoring temperature $T_{th}$ of the holder 11. The temperature controller 16 controls the Peltier element 12 by using the monitoring temperature $T_{th}$. As illustrated in FIG. 1, the thermistor 13 cannot be directly inserted into the sensor cell 31 to prevent leakage of gases through the sensor cell 31. Note that, although the thermistor 13 is used for detecting the monitoring temperature $T_{th}$ in the first embodiment, but other thermometers, such as a thermocouple and the like, may be used.

Figure 4:
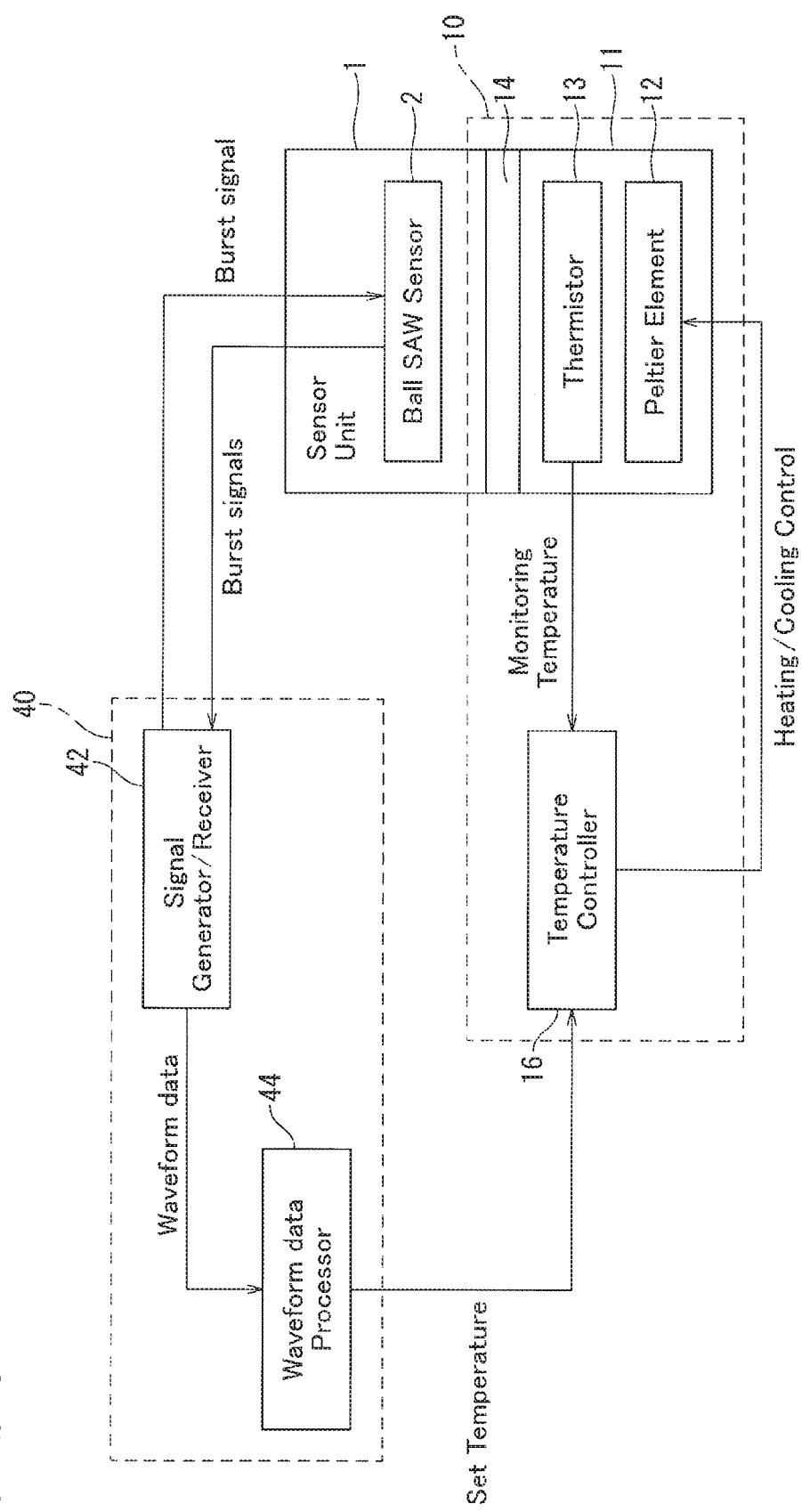
FIG. 4 is a block diagram illustrating an example of temperature control and signal transmission in the system for measuring the water concentration according to the first embodiment of the present invention.
Figure 5:
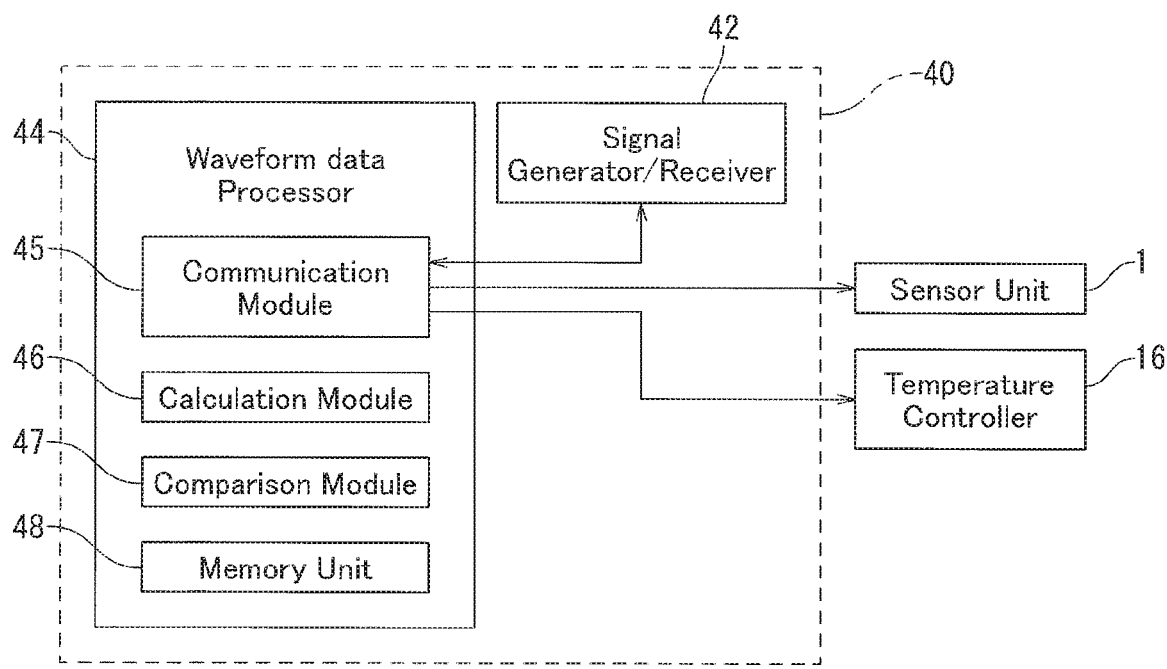
FIG. 5 is a block diagram illustrating an example of the signal processing unit in the system for measuring the water concentration according to the first embodiment of the present invention.

The signal processing unit 40, as illustrated in FIG. 4, includes a signal generator and a signal receiver (hereinafter the set of the signal generator and the signal receiver is referred as the "signal generator/receiver") 42 and a waveform data processor 44. The waveform data processor 44 includes a communication module (communication logical circuit) 45, a calculation module (calculation logical circuit) 46, a comparison module (comparison logical circuit) 47, and a memory unit 48 for logical hardware resources of a computer system, as illustrated in FIG. 5. The communication module 45 of the waveform data processor 44 sends a predetermined "set temperature" or a control temperature of the Peltier element 12 to the temperature controller 16 and instructions for flowing a gas into the sensor cell 31 to the sensor unit 1.

Moreover, the communication module 45 sends instructions to the signal generator/receiver 42 so that the signal generator/receiver 42 transmits a burst signal to the sensor electrode 22 of the ball sensor 2 so that the sensor electrode 22 can excite the collimated beam 21 of a SAW propagating around the piezoelectric ball 20, and receives burst signals of the collimated beam 21 through the sensor electrode 22 after the collimated beam 21 has propagated a predetermined number of turns around the piezoelectric ball 20. The signal generator/receiver 42 transmits waveform data of the burst signals to the waveform data processor 44.

The calculation module 46 of the waveform data processor 44 calculates the water concentration w and the ball temperature $T_B$ by using first and second relative changes in delay times of the first and second frequencies, respectively, using the waveform data of the burst signals. The comparison module 47 of the waveform data processor 44 compares the calculated ball temperature $T_B$ with the value of the previously measured ball temperature $T_B$ in order to determine whether the measurement has been implemented in thermal equilibrium. The memory unit 48 of the waveform data processor 44 stores a program for allowing the waveform data processor 44 to implement processing of the waveform data for calculating the water concentration w and the ball temperature $T_B$. Also, the memory unit 48 stores the set temperature of the Peltier element 12, the calculated ball temperature $T_B$, the previously measured ball temperature $T_B$, and data obtained during the calculation and analysis thereof during the operation of the waveform data processor 44.

The waveform data processor 44 may be part of central processing unit (CPU) of a general purpose computer system, such as a personal computer (PC) and the like. The waveform data processor 44 may include an arithmetic logic unit (ALU) that performs arithmetic and logic operations, a plurality of registers that supply operands to the ALU and store the results of ALU operations, and a control unit that orchestrates the fetching (from memory) and execution of instructions by directing the coordinated operations of the ALU. The communication module 45, the calculation module 46, and the comparison module 47 implementing the ALU may be discrete hardware resources such as logical circuit blocks or the electronic circuitry contained on a single integrated circuit (IC) chip, or alternatively, may be provided by virtually equivalent logical functions achieved by software, using the CPU of the general purpose computer system.

In addition, the program for the waveform data processor 44 for measuring the water concentration is not limited to being stored in the memory unit 48 which is installed in the waveform data processor 44. For example, the program may be stored in an external memory. Moreover, the program may be stored in a computer readable medium. By reading the computer readable medium in the memory unit 48 of the computer system, which includes the waveform data processor 44, the waveform data processor 44 implements coordinated operations for measuring water concentration, in accordance with a sequence of instructions recited in the program. Here, the "computer readable medium" refers to a recording medium or a storage medium, such as an external memory unit of a computer, a semiconductor memory, a magnetic disk, an optical disk, a magneto optical disk, and a magnetic tape, on which the program can be recorded.

The principle of measurement executed in the waveform data processor 44 will be described as follows, representing a first relative changes in delay time (DTC) by the Greek-alphabet as Delta-$t_1$, and a second relative DTC by the Greek-alphabet as Delta-$t_2$, as a macroscopic change in the value of a variable is represented by Greek-letter Delta in mathematics or science. Delta-$t_1$ is defined as Delta-Tau$_1$/Tau$_1$ at the first frequency $f_1$ and Delta-$t_2$ is defined as Delta-Tau$_2$/Tau$_2$ at the second frequency $f_2$. Here, the Greek-alphabets Tau$_1$ and Tau$_2$ are delay times of the SAW at the first and second frequencies $f_1$ and $f_2$, respectively, during propagating a predetermined number of turns without moisture adsorbed on the sensitive film 23, and Delta-Tau$_1$ and Delta-Tau$_2$ are delay time changes of the delay times Tau$_1$ and Tau$_2$ due to both the water concentration and the ball temperature change. Each of delay times Tau$_1$ and Tau$_2$ at each turn is obtained as a zero cross time closest to the maximum magnitude of a real part of wavelet transform of the received burst signals at the turns (refer to NPL 2).

The first and second relative changes Delta-$t_1$, Delta-$t_2$ are given by:

$$\text{Delta-}t_1 = B(T_B)f_1 G(w) + A_1(T_B - T_{REF}) \tag{1}$$

$$\text{Delta-}t_2 = B(T_B)f_2 G(w) + A_2(T_B - T_{REF}) \tag{2}$$

where $B(T_B)$ is a sensitivity factor, w is water concentration, $G(w)$ is a function of the water concentration, $T_B$ is the ball temperature of the ball sensor 2, $T_{REF}$ is a reference temperature, and $A_1$ and $A_2$ are temperature coefficients at frequencies $f_1$ and $f_2$, respectively.

From Eqs. (1) and (2), a first objective change Delta-$t_w$ in delay time due to gas concentration w is given by:

$$\text{Delta-}t_W = \text{Delta-}t_2 - C\text{Delta-}t_1 = (f_2 - Cf_1)B(T_B)G(w) \tag{3}$$

and, a second objective change Delta-$t_T$ in delay time due to the ball temperature (temperature term) $T_B$ is given by:

$$\text{Delta-}t_T = \{(f_2/f_1)\text{Delta-}t_1 - \text{Delta-}t_2\}/\{(f_2/f_1) - C\} = A_1(T_B - T_{REF}) \tag{4}$$

here $A_1$ and $A_2$ are temperature coefficients at the first and second frequencies $f_1$, $f_2$, respectively, and $C = A_2/A_1$ is temperature coefficient ratio. The water concentration w and the ball temperature $T_B$ can be simultaneously obtained by Eqs. (3) and (4), respectively.

Test measurements have been implemented using the fundamental wave and the third-order harmonic wave of the SAW, that is, $f_2 = 3f_1$, and without a gas flow. Each procedure of the test measurements will be described with reference to the flowchart illustrated in FIG. 6. In step S100, the signal generator/receiver 42a transmits the burst signal to the ball sensor 2, so as to exite the collimated beam 21 of the SAW. In step S101, after the collimated beam 21 has propagated a predetermined number of turns around the ball sensor 2, the signal generator/receiver 42 receives the burst signals of the collimated beam 21 through the ball sensor 2. Waveform data of the burst signals is transmitted to the waveform data processor 44.

In step S102, the waveform data processor 44 calculates the first and second relative changes Delta-$t_1$. Delta-$t_2$ of the first and second frequencies $f_1$, $f_2$, respectively, using the waveform data. Then, the first and second objective changes Delta-$t_W$, Delta-$t_T$ due to the water concentration w and the ball temperature $T_B$, respectively, are calculated using the first and second relative changes Delta-$t_1$, Delta-$t_2$. In step S103, the waveform data processor 44 calculates the ball temperature $T_B$ by Eq. (4) using the second objective change Delta-$t_T$. In step S104, a temperature change Delta-T of the ball temperature $T_B$ from the previous measurement cycle is compared with a threshold value Delta-Tc that is a criterion of thermal equilibrium. In the test measurements, the threshold value Delta-Tc is temporarily set as 20° C., the condition Delta-T<Delta-Tc is always satisfied for each measurement cycle of 12 seconds. In step S105, the gas concentration w is calculated by Eq. (3).

Figure 7:
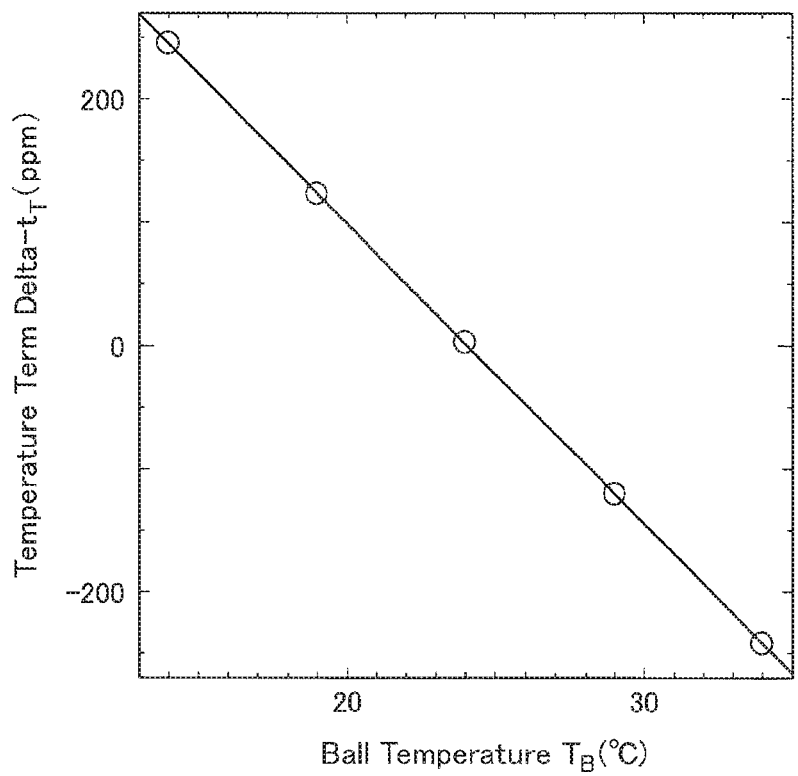
FIG. 7 is a diagram illustrating a relationship between the delay time change due to the ball temperature and the ball temperature according to the first embodiment of the present invention.

As a result of the test measurements, the temperature coefficient ratio C has been determined as C=0.9875 by least square fitting of the second relative change Delta-$t_2$ against the first relative change Delta-$t_1$. Further, as illustrated in FIG. 7, the second objective change Delta-$t_T$ has been plotted as a function of the ball temperature $T_B$, by changing the set temperature of the Peltier element 12. Here, the ball temperature $T_B$ has assumed to be identical to the monitoring temperature $T_{th}$ of the holder 11 when the gas flow rate v is zero. From Eq. (4), the temperature coefficient $A_1$ can be defined by the slope of the fitting line, and the reference temperature $T_{REF}$ can be defined by a particular ball temperature where the second objective change Delta-$t_T$ is zero. Thus, the temperature coefficient $A_1$ and the reference temperature $T_{REF}$ can be determined as -24.25 ppm/° C., and 24.06° C.

Substituting the temperature coefficient $A_1$ and the reference temperature $T_{REF}$ into Eq. (4), ball temperature $T_B$ can be obtained as;

$$T_B = 24.06 - 0.0412 \text{Delta-}t_T \quad (5)$$

The error of other ball temperatures calculated using Eq. (5) has been evaluated to be less than 0.24%. As mentioned above, according to the first embodiment, the ball temperature may be measured with high sensitivity and reliability.

Figure 8:
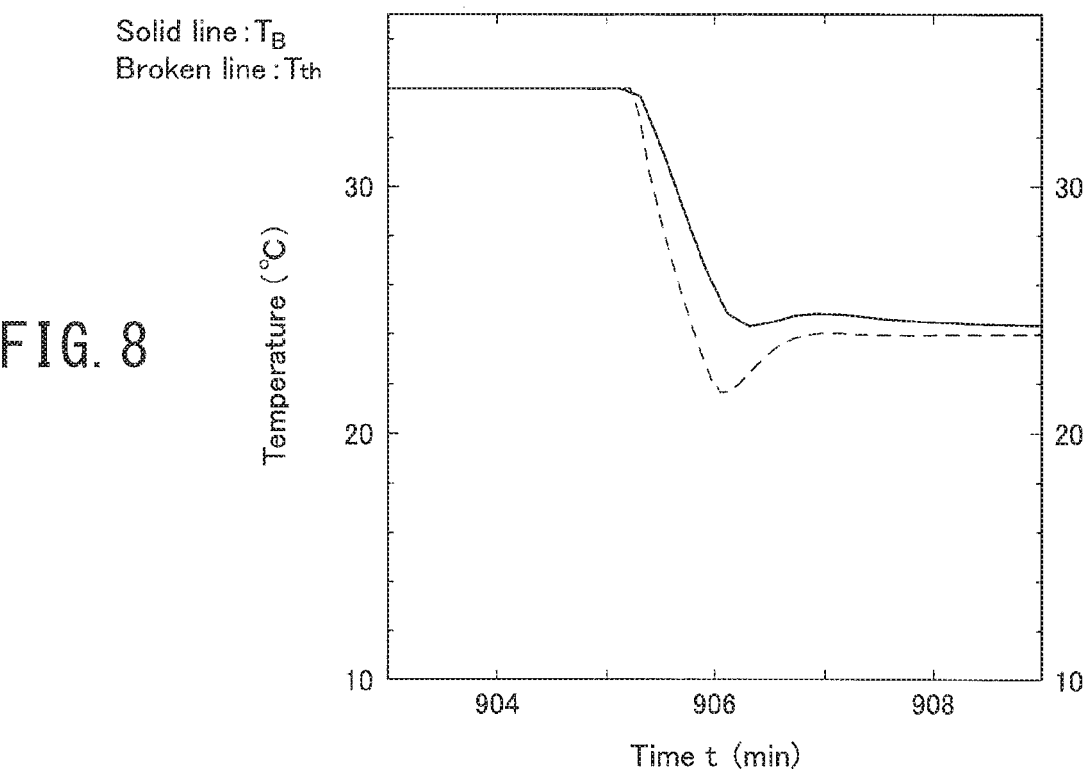
FIG. 8 is a diagram illustrating temperature jumps of the monitoring temperature and the ball temperature according to the first embodiment of the present invention.

In order to evaluate the effect of heat capacity of the sensor cell 31, the ball temperature $T_B$ calculated by Eq. (5) has been compared with the monitoring temperature $T_{th}$ measured by the thermistor 13. As illustrated in FIG. 8, when the specific set temperature of the Peltier element 12 has been changed from 34° C. to 24° C., the ball temperature $T_B$ has been delayed by about 0.5 minute from the monitoring temperature $T_{th}$ and has not reached 24° C. even after three minutes. This phenomenon is due to a large heat capacity of the adapter 14 made of stainless steel plate. Therefore, it is necessary to measure the water concentration with thermal equilibrium for precise measurement using viscoelastic property of the sensitive film 23. In order to avoid an error caused by the non-equilibrium phenomenon, it is desirable to set the threshold value Delta-Tc to a smaller value, for example 0.1° C. or less. On the contrary, it is desirable to set the threshold value Delta-Tc to a larger value, for example 10° C. or more, to continue measurement without interruption.

Figure 9:
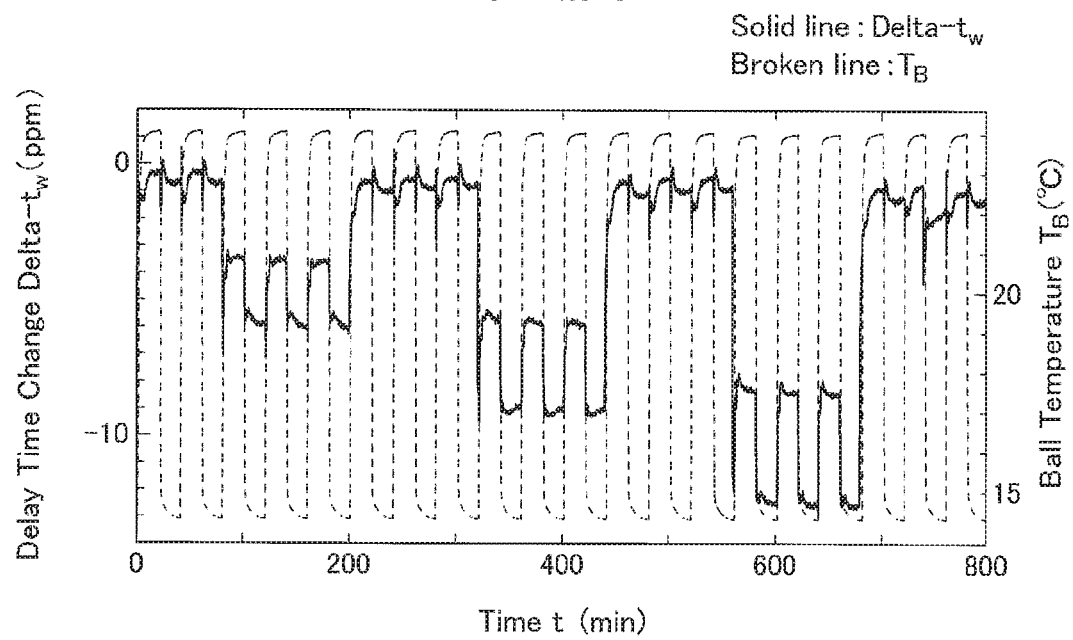
FIG. 9 is a diagram illustrating time changes of the delay time change due to the water concentration and the ball temperature while changing the water concentration and the set temperature according to the first embodiment of the present invention.
Figure 10:
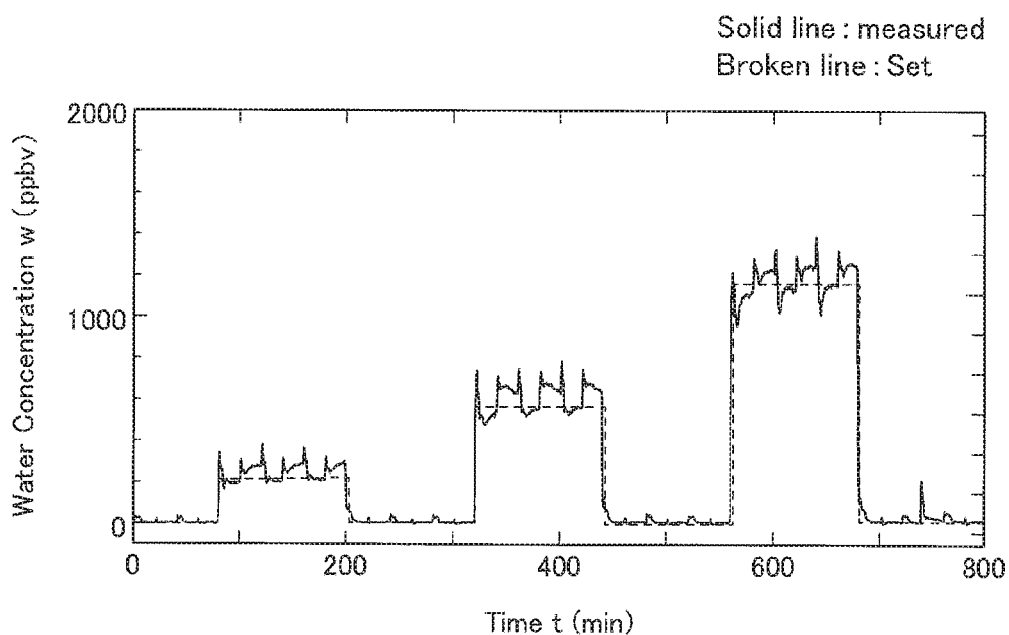
FIG. 10 is a diagram illustrating time changes of the set value of the water concentration and the measured value of the water concentration according to the first embodiment of the present invention.
Figures 11, 12:
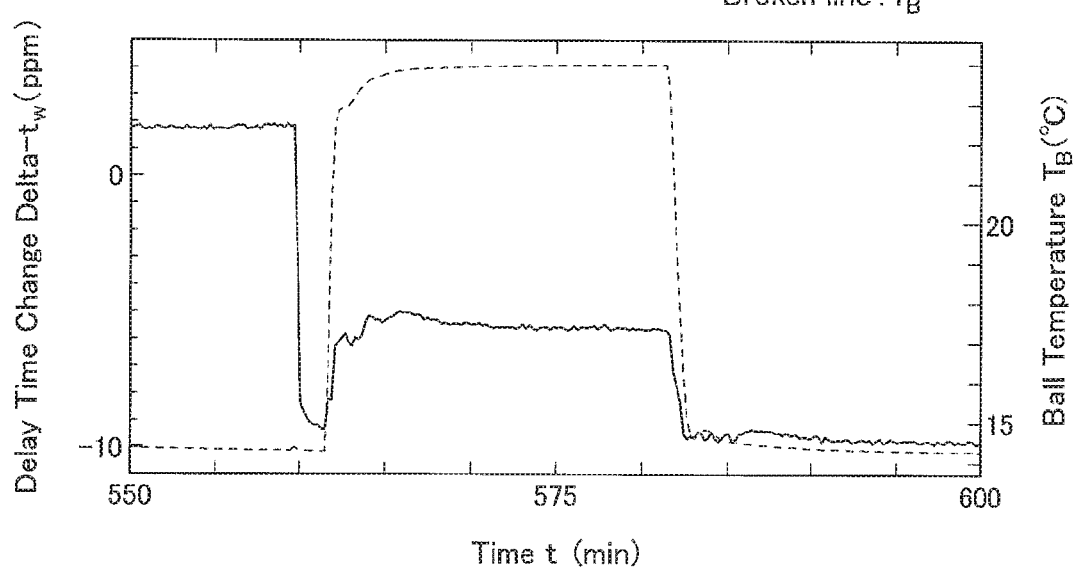
FIG. 11 is a table illustrating summarized results of FIGS. 9 and 10.
FIG. 12 is a diagram enlarging the range of time from 550 min to 600 min in FIG. 9.

As illustrated in FIG. 10, the water concentration w in a nitrogen ($N_2$) gas flow has been changed by the sequence of 1.3, 234, 1.3, 590, 1.3, 1180, 1.3 ppbv, where each water concentration w has been evaluated using the cavity ring down spectroscopy (CRDS) (refer to S. Hagihara, et al. Japanese Journal of Applied Physics, Vol. 53 (2014) 07KD08). At the same time, the set temperature of the Peltier element 12 has been changed between 24° C. and 14° C. The first objective change Delta-$t_w$ due to water concentration w and the ball temperature $T_B$ have been measured as illustrated in FIGS. 9 and 11. As illustrated in FIG. 9, the ball temperature $T_B$ has precisely reproduced the temperature setting, and not disturbed by the changes of the water concentration w, illustrating validity of Eq. (4) or (5). The first objective change Delta-$t_w$ has been changed with the water concentration w and also with the ball temperature $T_B$.

Using the first objective change Delta-$t_w$ in the Table illustrated in FIG. 11, the right hand side term in Eq. (3) may be evaluated as;

$$(f_2 - Cf_1)B(T_B) = a \exp[\text{Delta-}e/k_B(T_B+273)] \quad (6)$$

where $a = -6.33 \cdot L10^{-6}$, Delta-$e = 0.271$ (eV), $k_B = 8.617 \cdot L10^{-5}$ eV/K (Boltzmann Constant) and $$G(w) = w^{1/2} \quad (7)$$

Substituting Eqs. (6) and (7) into Eq.(3), the water concentration w can be obtained as;

$$w = (\text{Delta-}t_w/a)^2 \exp[-2\text{ Delta-}e/k_B(T_B+273)] \quad (8)$$

where $TB_B$ is given by Eq. (5). As illustrated in FIG. 10, the water concentration w has almost correctly reproduced the set value in the sequence. Therefore, according to the first embodiment, it is possible to achieve the concentration measurement even with varying temperature.

Figure 13:
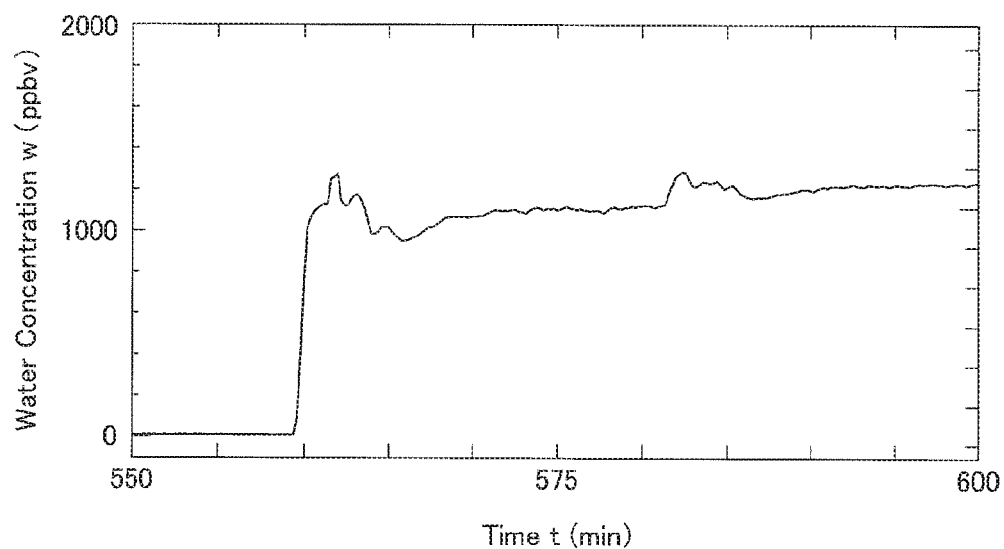
FIG. 13 is a diagram enlarging the range of time from 550 min to 600 min in FIG. 10.

FIG. 12 illustrates the transition of the first objective change Delta-$t_w$ and the ball temperature $T_B$ when the water concentration w has been changed from 1.3 to 1180 ppbv. As illustrated in FIG. 12, the first DTC Delta-$t_w$ has illustrated rather complex behavior due to the changes of water concentration w and the ball temperature $T_B$. However, as illustrated in FIG. 13, the water concentration w has almost correctly reproduced the set value.

Therefore, reliability of the concentration measurement even with varying temperature has been confirmed. However, the variation of the water concentration w near temperature jump where the ball temperature $T_B$ drastically changes between 14° C. and 24° C. is a subject matter to be solved for improvement of accuracy. The temperature jump may occur when the temperature change Delta-T of the ball temperature $T_B$ from the previous measurement cycle is larger than 0.1° C. Although the variation of the water concentration w might be due to adsorption and/or desorption of water in the sensor cell 31 and the tubing 36, the variation of the water concentration w may occur when the temperature change Delta-T of the ball temperature $T_B$ is too large.

To solve the problem of the variation of the water concentration w near the temperature jump, the other test measurement has been implemented with the threshold value Delta-Tc of 0.08° C. The water concentration w in the $N_2$ gas flow has been changed by the sequence of 3.39, 14.36, 3.39, 41.22, 3.39, 85.74, 3.39, 174.2, 3.39, 434.7, 3.39, 870.4, 3.39 ppbv, evaluated using the CRDS. At the same time, the ball temperature $T_B$ has been changed between 24° C. and 14° C. every 15 minutes by using the Peltier element 12.

Figure 14:
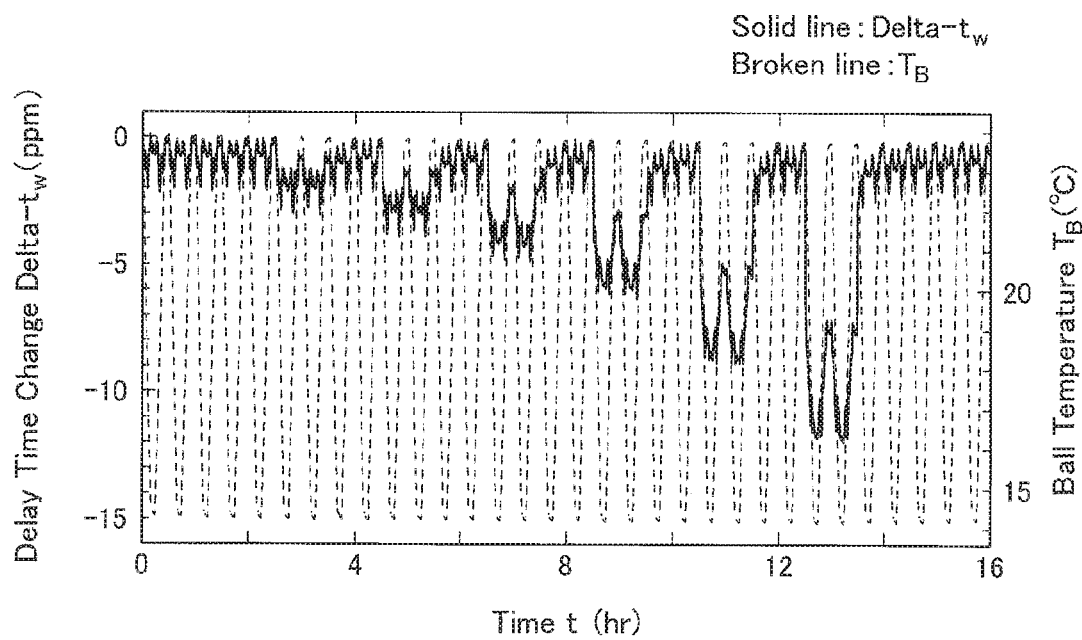
FIG. 14 is a diagram illustrating time changes of the delay time change due to the water concentration and the ball temperature while changing the water concentration and the set temperature according to the first embodiment of the present invention.
Figure 15:
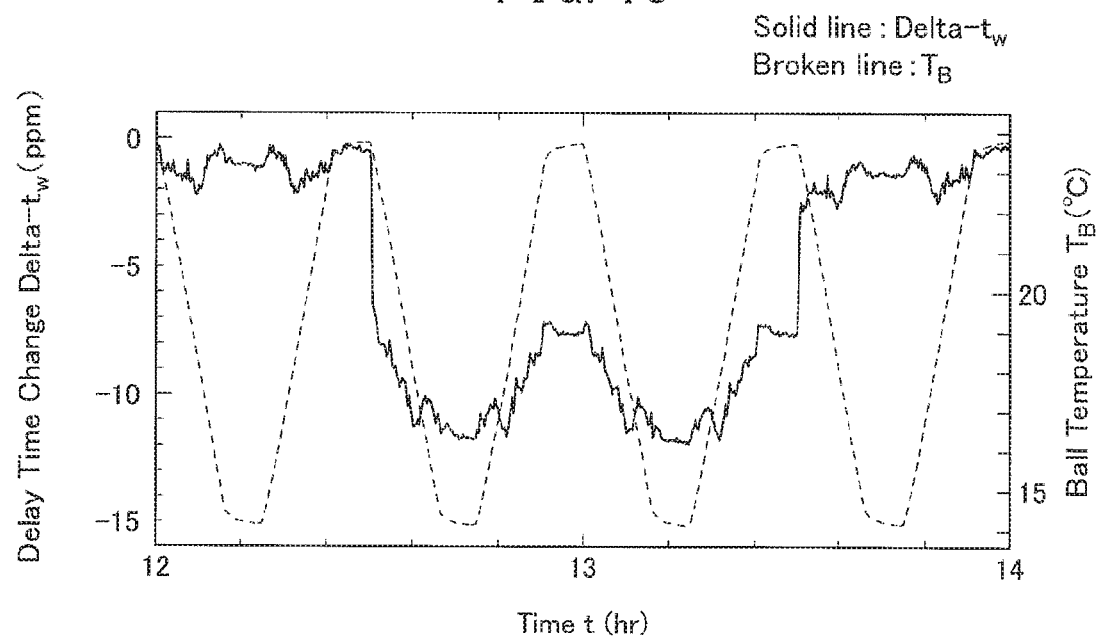
FIG. 15 is a diagram enlarging the range of time from 12 min to 14 min in FIG. 14.

As illustrated in FIG. 14, the measured ball temperature $T_B$ has reproduced the temperature setting. As illustrated in FIG. 15, it is known that the ball temperature $T_B$ has been kept at around 14° C. for about five minutes, changed from 14° C. to 24° C. in about ten minutes, and kept at around 24° C. for about five minutes. The first objective change Delta-$t_w$ due to the water concentration w has been changed with the water concentration w and also with the ball temperature $T_B$.

Figure 6:
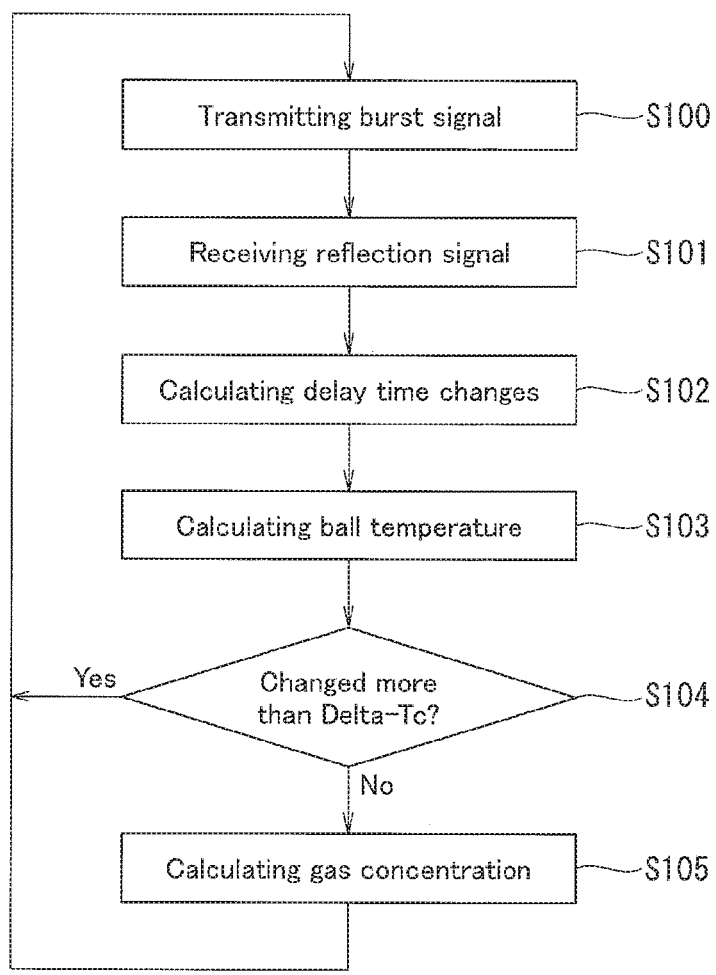
FIG. 6 is a flow chart illustrating an example of a method for measuring the water concentration according to the first embodiment of the present invention.
Figure 16:
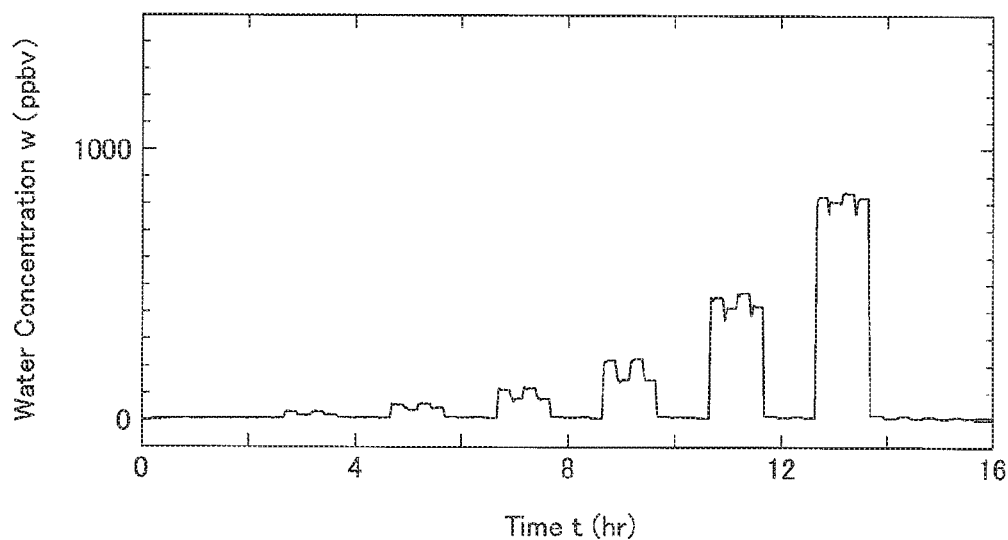
FIG. 16 is a diagram illustrating the water concentration evaluated from the results of FIG. 14.
Figure 17:
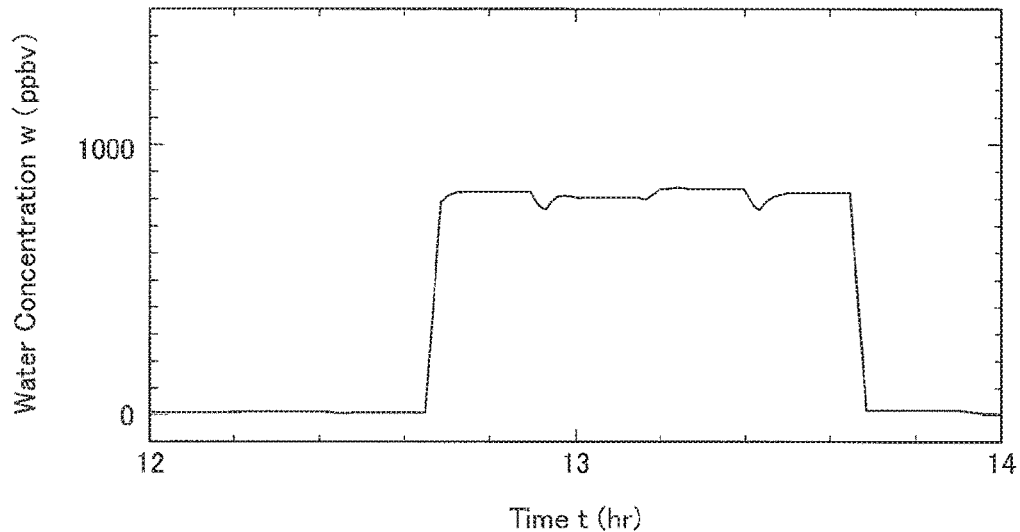
FIG. 17 is a diagram enlarging the range of time from 12 min to 14 min in FIG. 16.

The threshold value Delta-Tc has been set 0.08° C. in step S104 of the flow chart illustrated in FIG. 6, and the equilibrium condition Delta-T<Delta-Tc has been satisfied in the duration where the ball temperature $T_B$ has been kept at around 14° C. or 24° C. for about five minutes. In this case, the right hand side term of Eq. (3) may be evaluated as Eqs. (6) and (7) with $a = -9.00 \cdot L10^{-6}$, Delta-$e = 0.311$ (eV). Substituting Eqs. (6) and (7) with $a=-9.00'L10^{-6}$, Delta-e=0.311 (eV) into Eq.(3), the water concentration w can be obtained using Eq. (8). As illustrated in FIGS. 16 and 17, the variation of the measured water concentration w near the temperature jump can be decreased compared with that in FIGS. 10 and 13.

Figure 18:
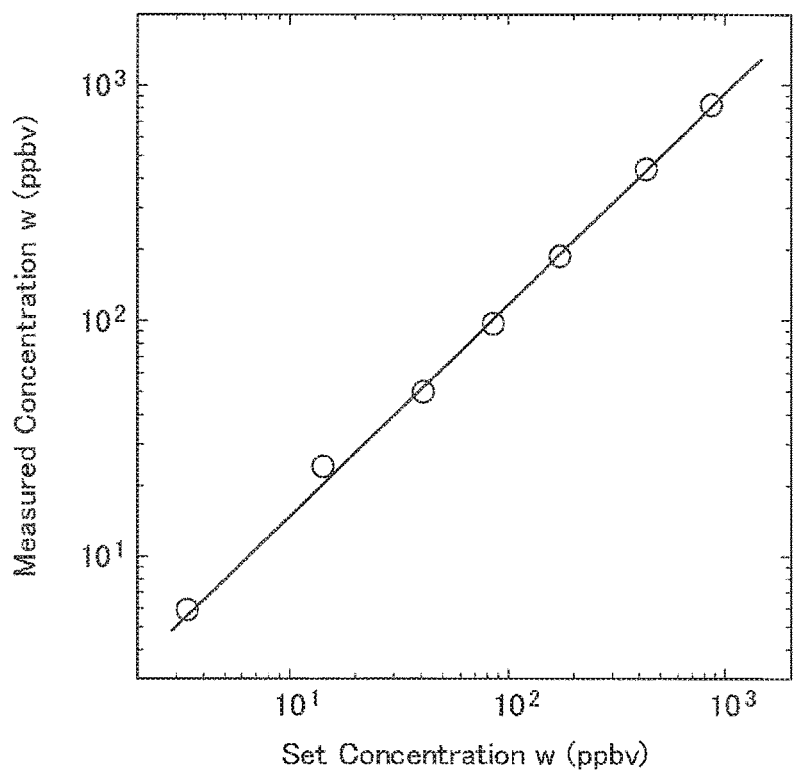
FIG. 18 is a diagram illustrating a relationship between the measured water concentration and the set water concentration obtained from FIG. 16.

FIG. 18 shows also comparison between the set concentration values, and measured concentration values averaged over 60 minutes. As illustrated in FIG. 18, it is understood that the agreement between set and measured concentration values is remarkable. Therefore, according to the first embodiment, it is possible to achieve reliability of the concentration measurement even under varying temperature.

(Measurement Method)

A measurement method of the water concentration according to the first embodiment will be described with reference to the flowchart illustrated in FIG. 6. First, the communication module 45 of the waveform data processor 44 transmits a specific set temperature of the Peltier element 12 to the temperature controller 16 illustrated in FIG. 1. The ball temperature is controlled by the Peltier element 12 with the specific set temperature, and the thermistor 13 inserted in the holder 11 monitors the temperature of the holder 11. In accordance with the instruction sent from the communication module 45, a gas containing water vapor is flowed into the sensor cell 31 through the tubing 36.

In step S100, in accordance with the instruction sent from the communication module 45, a burst signal is transmitted to the sensor electrode 22 from the signal generator/receiver 42, so as to exite the collimated beam 21 of the SAW. As illustrated in FIG. 2, the collimated beam 21 propagates repeatedly through the orbital path on the piezoelectric ball 20 while passing through the sensitive film 23 allocated on the orbital path.

In step S101, after the collimated beam 21 has propagated a predetermined number of turns, for example 50 turns, around the piezoelectric ball 20, the signal generator/receiver 42 receives burst signals of the collimated beam 21 through the sensor electrode 22. Through the communication module 45, waveform data of the burst signals is transmitted to the waveform data processor 44 illustrated in FIG. 4.

In step S102, the calculation module 46 of the waveform data processor 44 calculates the first and second relative changes Delta-$t_1$, Delta-$t_2$ of the first and second frequencies $f_1$, $f_2$, respectively, by the waveform data of the burst signals. Then, the first and second objective changes Delta-$t_W$, Delta-$t_T$ due to the water concentration w and the ball temperature $T_B$, respectively, are calculated using the first and second relative changes Delta-$t_1$, Delta-$t_2$.

In step S103, the calculation module 46 of the waveform data processor 44 calculates the ball temperature $T_B$ using the second objective change Delta-$t_T$.

In step S104, a temperature change Delta-T of the ball temperature $T_B$ from the previous measurement cycle is compared with a threshold value Delta-Tc by the comparison module 47 of the waveform data processor 44. In the concentration measurement according to the first embodiment, the threshold value Delta-Tc is set as 0.08° C.

When the temperature change Delta-T is equal to or smaller than the threshold value Delta-Tc, in step S105, the gas concentration w is calculated by the calculation module 46 and recorded in the memory unit 48 as a new measured value. On the other hand, when the temperature change Delta-T is larger than the threshold value Delta-Tc, it is determined that the thermal equilibrium needed for precise measurement of viscoelastic property of the sensitive film is not realized. Thus, the water concentration w in the previous cycle is still effective, and processing returns to step S100, so as to start a next cycle of the measurement.

In the measurement method according to the first embodiment, the water concentration w and the ball temperature $T_B$ of the ball sensor 2 can be simultaneously measured with high sensitivity and reliability even under varying temperature.

Second Embodiment

As illustrated in FIG. 8, the change of the ball temperature $T_B$ is rather slow and delayed by about 0.5 minute compared with the monitoring temperature $T_{th}$ of the thermistor 13 in the first embodiment. Moreover, the ball temperature $T_B$ may not reach the desired set temperature even after three minutes. One of the reasons is the large heat capacity of the adapter 14 made of stainless steel plate. Moreover, in order to monitor the ball temperature $T_B$, the thermistor 13 should be installed as close to the ball sensor 2 as possible. However, since leakage of moisture from the outside air should be avoided, the thermistor 13 cannot be installed in the sensor cell 31.

As mentioned in the first embodiment, the ball temperature $T_B$ is available using the delay times $Tau_1$ and $Tau_2$ of the SAW and the relative changes Delta-$Tau_1$ and Delta-$Tau_2$ of the delay times $Tau_1$ and $Tau_2$. More specifically, the ball temperature $T_B$ calculated by the waveform data processor 44 may be used to control the Peltier element 12 instead of the monitoring temperature $T_{th}$ by the thermistor 13. Thus, the ball sensor 2 itself may be used as a precise thermometer to monitor the ball temperature $T_B$.

Consequently, performance of the temperature control process may be ideal and the response of the ball temperature $T_B$ can be significantly faster. The temperature control requires the use of the ball temperature $T_B$ as a control signal, and when the ball temperature $T_B$ is used as the control signal, the performance of the system for measuring water concentration pertaining to the first embodiment can be improved, compared with the configuration, in which the commercial temperature controller is used. This improvement is realized using an apparatus illustrated in FIG. 19.

In a second embodiment of the present invention, as illustrated in FIG. 19, the temperature controller 16 includes a command interpreter 18 for receiving a specific set temperature of the Peltier element 12 and a calculated ball temperature $T_B$ from the waveform data processor 44. The second embodiment differs from the first embodiment in that the command interpreter 18 is provided in the waveform data processor 44. Other configurations are almost same as in the first embodiment, so duplicated descriptions are omitted.

During measurement, the waveform data processor 44 sets a temperature in the temperature controller 16 for controlling the Peltier element 12. The signal generator/receiver 42 transmits a burst signal to the ball sensor 2, and receives burst signals of the collimated beam 21 after the collimated beam 21 has propagated a predetermined number of turns around the piezoelectric ball 20. Subsequently, the signal generator/receiver 42 sends the waveform data of the burst signals to the waveform data processor 44. The waveform data processor 44 applies a signal processing to the waveform data using Eqs. (4) and (5), so as to obtain a ball temperature $T_B$ as a calculated temperature. The calculated ball temperature $T_B$ is sent to the command interpreter 18 using the Recommended Standard 232 version C (RS232C) communication protocol defined by the Electronic Industries Association (EIA).

When the calculated ball temperature $T_B$ is lower or higher than the set temperature, the temperature controller 16 sends a heating or cooling current to the Peltier element 12 in accordance with the proportional-integral-differential (PID) control algorithm. In the second embodiment, since the ball temperature $T_B$ is used as a control signal for controlling the Peltier element 12, the response of the ball temperature $T_B$ may be significantly faster compared with using the monitoring temperature $T_{th}$ monitored by the thermistor 13.

Figure 20A:
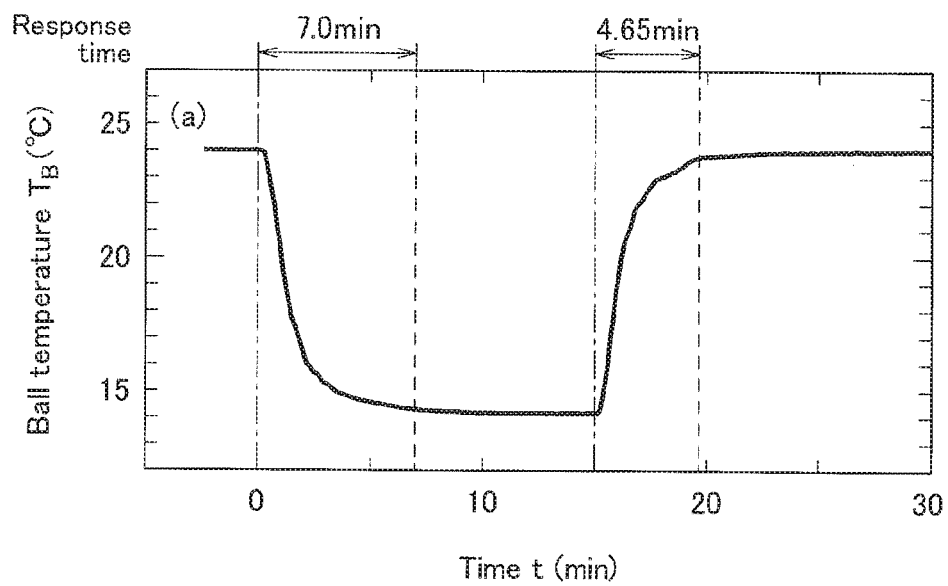
FIG. 20A is a diagram illustrating the time changes of the ball temperature according to the first embodiment of the present invention.
Figure 20B:
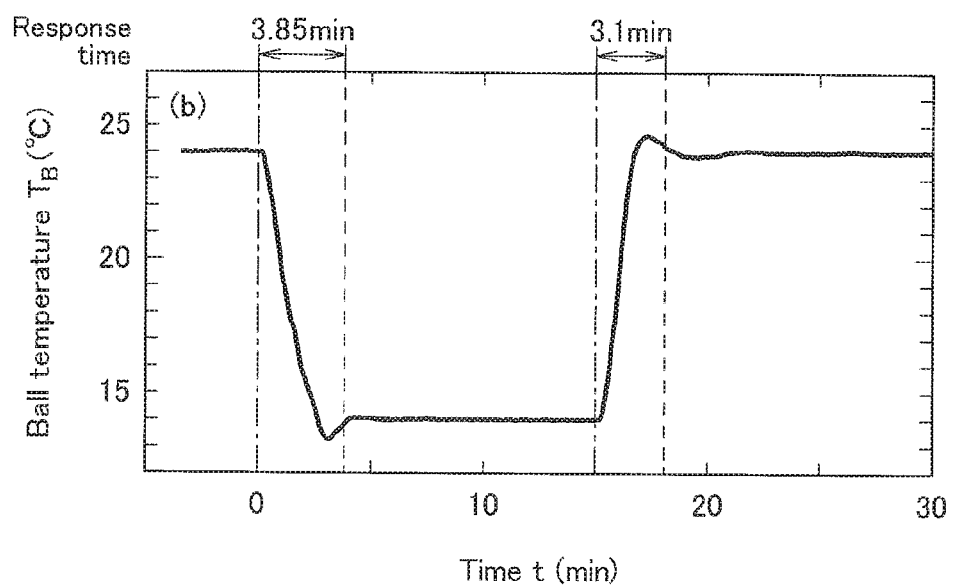
FIG. 20B is a diagram illustrating the time changes of the ball temperature according to the second embodiment of the present invention.

The response time has been evaluated by the time required to reach the specific set temperature and to be stabilized within the temperature range of ±0.2° C. from the set temperature. FIGS. 20A and 20B illustrate the time changes of the ball temperature $T_B$ controlled by the Peltier element 12 when changing the specific set temperature of the Peltier element 12 from 24° C. to 14° C. at time t=0 min, and from 14° C. to 24° C. at time t=15 min. FIG. 20A illustrates the temperature control according to the first embodiment, in which the monitoring temperature $T_{th}$ by the thermistor 13 has been used as a control signal. FIG. 20B illustrates the temperature control according to the second embodiment, in which the calculated ball temperature $T_B$ by the waveform data processor 44 has been used as a control signal.

As illustrated in FIG. 20A, the response time is about 7.0 min when the specific set temperature has been changed from 24° C. to 14° C., and about 4.65 min when the specific set temperature has been changed from 14° C. to 24° C., respectively. As illustrated in FIG. 20B, the response time is about 3.85 min when the specific set temperature has been changed from 24° C. to 14° C., and about 3.1 min when the specific set temperature has been changed from 14° C. to 24° C., respectively. Thus, it is understood from FIGS. 20A and 20B, that the response of the ball temperature $T_B$ using the ball temperature $T_B$ as a control signal may be significantly faster compared with using the monitoring temperature $T_{th}$ monitored by the thermistor 13.

Other Embodiments

As mentioned above, the present invention has been described on the basis of the first and second embodiments. However, the discussions and drawings that configure a part of this disclosure should not be understood to limit the present invention. From this disclosure, various variations, implementations and operational techniques would be evident for one skilled in the art.

In the first and second embodiments, the temperature control unit 10 is used for controlling temperature of the ball sensor 2. However, when measurement is implemented at room temperature or in the temperature controlled chamber, the temperature control for the ball sensor 2 is not always necessary. In such cases, the measurement system may include the sensor unit 1 and the signal processing unit 40.

The trace moisture sensor has been described as a gas sensor in the first and second embodiments. However, the present invention is applicable not only to the trace moisture sensor but also to sensors for various kinds of gas molecules, such as hydrogen molecules, oxygen molecules, volatile organic compound molecules, and the like. For example, for a sensitive film 23 of a hydrogen gas sensor, a palladium (Pd) film or a Pd compound film may be used. In this way, the present invention naturally includes various embodiments that are not noted here. Thus, the technical scope of the present invention is determined only by the "special technical features" prescribed in claims that are reasonable from the above-mentioned descriptions.

REFERENCE SIGNS LIST 1 sensor unit
2 ball sensor (ball SAW sensor)
10 temperature control unit
11 holder
12 Peltier element
13 thermistor
14 adapter
16 temperature controller
18 command interpreter
20 piezoelectric ball
21 collimated beam
22 sensor electrode
23 sensitive film
31 sensor cell
32 electrode-holder base
33 sensor-cell cap
34 electrode holder
35 external electrode
36 tubing
40 signal processing unit
42 signal generator/receiver (signal generator and receiver)
44 waveform data processor
45 communication module
46 calculation module
47 comparison module
48 memory unit

The invention claimed is:

1. A system for measuring a gas concentration, comprising:
a ball sensor having:
a piezoelectric ball,
a sensor electrode configured to generate a collimated beam of a surface acoustic wave including a fundamental wave of a first frequency and a harmonic wave of a second frequency, which propagates through an orbital path on the piezoelectric ball, and
a sensitive film deposited on the piezoelectric ball, configured to adsorb a target gas, the sensitive film is arranged in a position where the collimated beam of the surface acoustic wave passes through; and
a signal processing unit having:
a signal generator configured to transmit a burst signal to the sensor electrode so as to excite the collimated beam propagating around the piezoelectric ball,
a signal receiver configured to receive burst signals of the collimated beam through the sensor electrode after the collimated beam has propagated a predetermined number of turns around the piezoelectric ball, and
a waveform data processor configured to calculate the gas concentration of the target gas and the ball temperature by first and second relative changes in delay times of the first and second frequencies, respectively, using waveform data of the burst signals.

2. The system of claim 1, wherein, when calculating the gas concentration and the ball temperature, the waveform data processor calculates first and second objective changes in delay times by the first and second relative changes, the first objective change due to the gas concentration, the second objective change due to the ball temperature.

3. The system of claim 1, wherein the first relative change is calculated using a delay time of the fundamental wave and a change in the delay time of the fundamental wave due to both the gas concentration and the ball temperature, and
the second relative change is calculated using a delay time of the harmonic wave and a change in the delay time of the harmonic wave due to both the gas concentration and the ball temperature.

4. The system of claim 3, wherein the first and second relative changes are given by, Delta-$t_1$=Delta-Tau$_1$/Tau$_1$, and Delta-$t_2$=Delta-Tau$_2$/Tau$_2$, here, Delta-$t_1$ and Delta-$t_2$ are the first and second relative changes at the first and second frequencies, respectively, Tau$_1$ and Tau$_2$ are the delay times of the fundamental wave and the harmonic wave, respectively, and Delta-Tau$_1$ and Delta-Tau$_2$ are the changes in delay times of the fundamental wave and the harmonic wave, respectively.

5. The system of claim 4, wherein the first and second objective changes are given by, Delta-$t_W$=Delta-$t_2$−CDelta-$t_1$, and Delta-$t_T$={$(f_2/f_1)$Delta-$t_1$−Delta-$t_2$}/{$(f_2/f_1)$−C}, here, Delta-$t_w$ and Delta-$t_T$ are the first and second objective changes, respectively, $f_1$ and $f_2$ are the first and second frequencies, respectively, C=$A_2/A_1$ is temperature coefficient ratio, and $A_1$ and $A_2$ are temperature coefficients at the first and second frequencies, respectively, and wherein the ball temperature $T_B$ is given by Delta-$t_T$=$A_1$ ($T_B$−$T_{REF}$)

here, $T_{REF}$ is a reference ball temperature where the second objective change Delta-$t_T$ is zero.

6. The system of claim 1, wherein the harmonic wave is a third-order harmonic wave or a fifth-order harmonic wave.

7. The system of claim 1, wherein the target gas is water vapor and the sensitive film is a silica film.

8. The system of claim 1, further comprising a temperature control unit configured to control a ball temperature of the ball sensor.

9. The system of claim 8, wherein the temperature control unit includes:
a Peltier element for heating and cooling the ball sensor,
a thermistor for detecting a monitoring temperature of the Peltier element, and
a temperature controller for controlling the Peltier element by using the monitoring temperature.

10. The system of claim 8, wherein the temperature control unit includes:
a Peltier element for heating and cooling the ball sensor,
a temperature controller for controlling the Peltier element by using the calculated ball temperature.

11. A method for measuring a gas concentration using a ball sensor having a sensor electrode generating a surface acoustic wave and a sensitive film adsorbing a target gas, on a piezoelectric ball, comprising:

flowing a gas containing the target gas into a sensor cell having the ball sensor in place;
transmitting a burst signal to the sensor electrode so as to excite a collimated beam of the surface acoustic wave including a fundamental wave of a first frequency and a harmonic wave of a second frequency, which propagates repeatedly through an orbital path on the piezoelectric ball while passing through the sensitive film deposited on the orbital path;
receiving burst signals of the collimated beam through the sensor electrode after the collimated beam has propagated a predetermined number of turns around the piezoelectric ball; and
calculating first and second relative changes in delay times of the first and second frequencies, respectively, by waveform data of the burst signals so as to calculate the gas concentration of the target gas and the ball temperature.

12. The method of claim 11, further comprising:
after calculating the ball temperature, comparing a temperature change between the ball temperature and a previously measured ball temperature with a threshold value; and
when the temperature change is equal to or less than the threshold value, calculated values of the gas concentration and the ball temperature are recorded as measured values.

13. The method of claim 11, wherein, when calculating the gas concentration and the ball temperature, a first objective change in the delay time due to the gas concentration and a second objective change in the delay time due to the ball temperature are calculated using the first and second relative changes.

14. The method of claim 11, wherein the first relative change is calculated using a delay time of the fundamental wave and a change in the delay time of the fundamental wave due to both the gas concentration and the ball temperature, and
the second relative change is calculated using a delay time of the harmonic wave and a change in the delay time of the harmonic wave due to both the gas concentration and the ball temperature.

15. The method of claim 14, wherein the first and second relative changes are given by, Delta-$t_1$=Delta-Tau$_1$/Tau$_1$, and Delta-$t_2$=Delta-Tau$_2$/Tau$_2$, here, Delta-$t_1$ and Delta-$t_2$ are the first and second relative changes at the first and second frequencies, respectively, Tau$_1$ and Tau$_2$ are the delay times of the fundamental wave and the harmonic wave, respectively, and Delta-Tau$_1$ and Delta-Tau$_2$ are the changes in delay times of the fundamental wave and the harmonic wave, respectively.

16. The method of claim 15, wherein the first and second objective changes are given by, Delta-$t_W$=Delta-$t_2$−CDelta-$t_1$, and Delta-$t_T$={$(f_2/f_1)$Delta-$t_1$−Delta-$t_2$}/{$(f_2/f_1)$−C}, here, Delta-$t_w$ and Delta-$t_T$ are the first and second objective changes, respectively, $f_1$ and $f_2$ are the first and second frequencies, respectively, C=$A_2/A_1$ is temperature coefficient ratio, and $A_1$ and $A_2$ are temperature coefficients at the first and second frequencies, respectively, and wherein the ball temperature $T_B$ is given by $$\text{Delta-}t_T = A_1 (T_B - T_{REF})$$

here, $T_{REF}$ is a reference ball temperature where the second objective change Delta-$t_T$ is zero.

17. The method of claim 11, wherein the harmonic wave is a third-order harmonic wave or a fifth-order harmonic wave.

18. The method of claim 11, wherein the target gas is water vapor and the sensitive film is a silica film.

19. The method of claim 11, further comprising, before flowing the gas, controlling the ball temperature of the ball sensor to a set temperature.

20. A computer program product embodied on a non-transitory computer-readable medium for measuring a gas concentration using a ball sensor having a sensor electrode generating a surface acoustic wave and a sensitive film adsorbing a target gas, on a piezoelectric ball, the computer program product comprising:

instructions to flow a gas containing the target gas into a sensor cell having the ball sensor in place;

instructions to transmit a burst signal to the sensor electrode so as to excite a collimated beam of the surface acoustic wave including a fundamental wave of a first frequency and a harmonic wave of a second frequency, which propagates repeatedly through an orbital path on the piezoelectric ball while passing through the sensitive film deposited on the orbital path;

instructions to receive burst signals of the collimated beam through the sensor electrode after the collimated beam has propagated a predetermined number of turns around the piezoelectric ball; and instructions to calculate first and second relative changes in delay times of the first and second frequencies, respectively, by waveform data of the burst signals so as to calculate the gas concentration of the target gas and the ball temperature.

\* \* \* \* \*